United States Patent
Gazzetto et al.

(10) Patent No.: US 12,384,802 B2
(45) Date of Patent: *Aug. 12, 2025

(54) MANUFACTURING OF DIMERIC CONTRAST AGENT

(71) Applicant: BRACCO IMAGING S.P.A., Milan (IT)

(72) Inventors: Sonia Gazzetto, Cascinette d'Ivrea (IT); Valeria Boi, Strambino (IT); Andrea Banin, Collegno (IT); Andrea Barale, Bibiana (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 18/719,054

(22) PCT Filed: Dec. 13, 2022

(86) PCT No.: PCT/EP2022/085615
§ 371 (c)(1),
(2) Date: Jun. 12, 2024

(87) PCT Pub. No.: WO2023/110867
PCT Pub. Date: Jun. 22, 2023

(65) Prior Publication Data
US 2024/0425527 A1    Dec. 26, 2024

(30) Foreign Application Priority Data
Dec. 14, 2021 (EP) .................... 21214327

(51) Int. Cl.
| | |
|---|---|
| C07D 403/12 | (2006.01) |
| A61K 49/10 | (2006.01) |
| C07D 257/02 | (2006.01) |
| C07F 5/00 | (2006.01) |

(52) U.S. Cl.
CPC .................. C07F 5/003 (2013.01)

(58) Field of Classification Search
CPC ... C07D 257/02; C07D 403/12; A61K 49/108
See application file for complete search history.

(56) References Cited

U.S. PATENT DOCUMENTS

| | | | |
|---|---|---|---|
| 2012/0082624 A1* | 4/2012 | Port | A61K 49/06 424/9.363 |
| 2018/0362511 A1* | 12/2018 | Boi | C07D 257/02 |
| 2023/0303592 A1 | 9/2023 | Barale et al. | |

FOREIGN PATENT DOCUMENTS

| | | |
|---|---|---|
| WO | 2017098044 A1 | 6/2017 |
| WO | 2021116165 A1 | 6/2021 |

OTHER PUBLICATIONS

Chappell et al. Nuclear Medicine and Biology 2003, 30, 581-595.*
Co-pending U.S. Appl. No. 18/017,939, filed Jan. 25, 2023.*
Co-pending U.S. Appl. No. 18/565,770, filed Nov. 30, 2023.*
Co-pending U.S. Appl. No. 18/566,057, filed Nov. 30, 2023.*
Co-pending U.S. Appl. No. 18/718,945, filed Jun. 12, 2024.*
Bhumasamudram, J. et al., "On the synthesis of 1,4,7-tris(butoxycarbonylmethyl)-1,4,7,10-tetraazacyclododecane", Tetrahedron Letters, 52:2058-2061 (2011).
Greene, T.W., "Protective groups in organic synthesis," Chapter 5, pp. 533-646, John Wiley & Sons, Inc. (2007).
International Search Report and Written Opinion for PCT/EP2022/085615, mailed Mar. 14, 2023.
Moore, D.A., "Selective Trialkylation of Cyclen With tert-Butyl Bromoacetate [1,4,7,10-Tetraazacyclododecane-1,4,7-triacetic acid, Tri-tert-butyl Ester Hydrobromide]," Org. Synth., 85:10-14 (2008).

* cited by examiner

*Primary Examiner* — Irina Neagu
(74) *Attorney, Agent, or Firm* — VIVICAR Law, PLLC

(57) ABSTRACT

The invention relates to a process for the preparation of the gadolinium dimeric contrast agent [p-[1-[bis[2-(hydroxy-KO)-3-[4,7,10-tris[(carboxy-KO)methyl]-1,4,7,10-tetraazacyclododec-1-yl-K/V1,K/V4,K/V7,K/V10]propyl]amino]-1-deoxy-D-glucitolato(6-)]]di-gadolinium complex. Such process includes preparation steps carried out one-pot and without isolation of the obtained intermediates. The gadolinium dimeric contrast agent can be for use in diagnostic imaging, in particular in Magnetic resonance Imaging (MRI).

21 Claims, No Drawings

MANUFACTURING OF DIMERIC CONTRAST AGENT

CROSS-REFERENCE TO RELATED APPLICATIONS

This application is the national stage application of corresponding international application number PCT/EP2022/085615, filed Dec. 13, 2022, which claims priority to and the benefit of European application no. 21214327.5, filed Dec. 14, 2021, which is hereby incorporated by reference in its entirety.

FIELD OF THE INVENTION

The present invention relates to the preparation of [μ-[1-[bis[2-(hydroxy-κO)-3-[4,7,10-tris[(carboxy-κO)methyl]-1,4,7,10-tetraazacyclododec-1-yl-κ$N^1$,κ$N^4$,κ$N^7$,κ$N^{10}$]propyl]amino]-1-deoxy-D-glucitolato(6-)]]di-Gadolinium complex, which can be used as a contrast agent in Magnetic Resonance Imaging (MRI).

STATE OF THE ART

Magnetic Resonance Imaging (MRI) is a well-known diagnostic imaging technique that is used in clinical diagnostics for a growing number of indications.

Gadolinium (Gd(III)) complexes are commonly used as contrast agents in MRI due to their long relaxation times.

WO2017/098044 (same applicant as the present application) discloses dimeric paramagnetic complexes useful as contrast agents MRI. Among a number of specific compounds, the application discloses the di-gadolinium complex of the 1-[bis[2-hydroxy-3-[4,7,10-tris(carboxymethyl)-1,4,7,10-tetraazacyclododec-1-yl]propyl]amino]-1-deoxy-D-glucitol ligand of formula

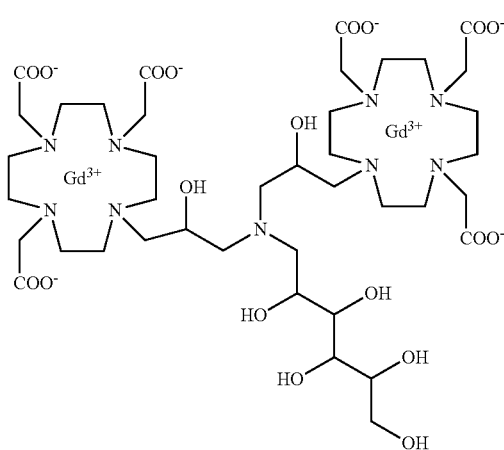

hereinafter otherwise identified as "dimeric complex compound 5" or, more simply as "Compound 5". Compound 5 shows interesting properties, especially in terms of relaxivity and tolerability that makes it suitable for use in the in vivo diagnostic imaging carried out with doses of the paramagnetic complex lower than those required by the contrast agents of the market.

WO2017/098044 further discloses the following process for the synthesis of Compound 5 (Scheme 1):

Scheme 1

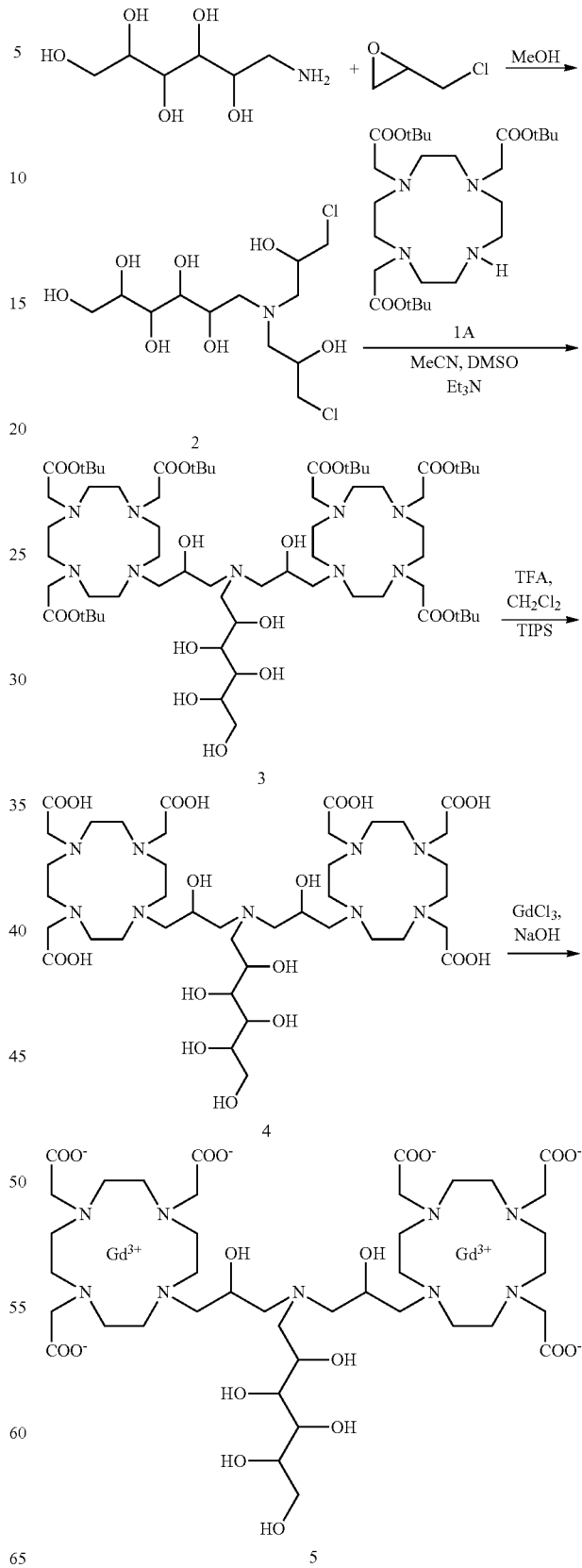

The main steps disclosed in WO2017/098044 process comprise:
a) preparation and isolation of DO3A tri-tert-butyl ester (compound 1A) carried out substantially as disclosed in *Org. Synth.* 2008, 85, 10;
b) preparation of the intermediate 2 by alkylation of D-glucamine with epichlorohydrin (molar ratio 1:4.95) in MeOH at 50° C. for 26 h, and the isolation of the condensation product by evaporation of the crude reaction;
c) alkylation of DO3A tri-tert-butyl ester 1A with the intermediate 2 in DMSO and Et₃N, evaporation and purification of the crude residue on Amberlite XAD® 1600 leading to give the protected ligand 3;
d) deprotection of the protected ligand 3 with TFA acid and TIPS in dichloromethane, evaporation of the crude reaction and purification of the residue on Amberlite XE 750;
e) complexation of the ligand 4 in water with gadolinium chloride hexahydrate, and purification on Amberchrome CG161M resin of the crude product obtained by filtration and evaporation of the solution.

The process disclosed in WO2017/098044 requires the synthesis and isolation of each of the individual intermediates, which is generally carried out by evaporation to residue of the solvent. Such isolation steps, besides being unsuitable for a large-scale production, unavoidably result in a reduction in the overall yield and efficiency of the process.

Moreover, the process disclosed in WO2017/098044 is not particularly suitable for working on larger scales, for example on industrial processes, because it encompasses the use of harsh materials that are difficult to handle, such TFA, TIPS and DCM, which might i.a. cause corrosion and thus wear out the synthesis apparatuses and/or might not be safe for the health of the workers.

SUMMARY OF THE INVENTION

The present invention generally relates to an optimized process for the manufacturing of the dimeric complex compound 5 which includes preparation steps carried out one-pot and without isolation of the resulting intermediates, allowing for both time-savings and an improved overall yield and efficiency.

More particularly, the invention relates to process for the manufacturing of the dimeric complex compound 5 of formula

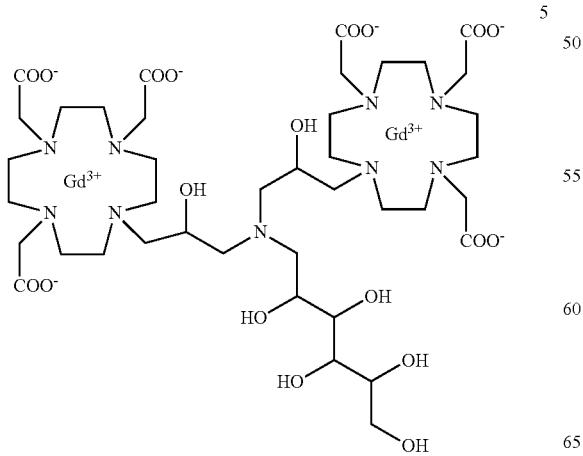

comprising the following steps:

a) admixing a salt of the DO3A tri-tert-butyl ester of formula 1B

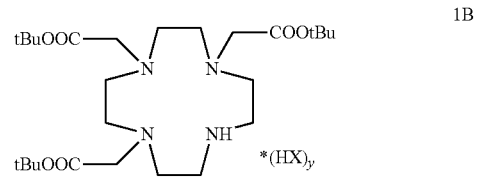

wherein X is a halogen anion, preferably selected from the group consisting of chloride, bromide, and iodide, and y is an integer from 1 to 3, preferably y is 1;

with a basic aqueous solution and an organic solvent immiscible with the basic aqueous solution, to provide a heterogeneous mixture comprising the salt 1B; thereby b) converting the salt 1B of step a), to provide a heterogenous mixture comprising DO3A tri-tert-butyl ester of formula 1A

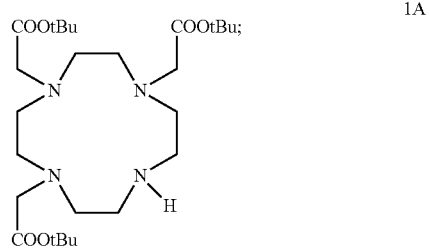

c) collecting the organic solvent from the heterogeneous mixture of step b), to obtain an organic solution comprising DO3A tri-tert-butyl ester of formula 1A;

d) preparing a solution comprising a compound of formula 2

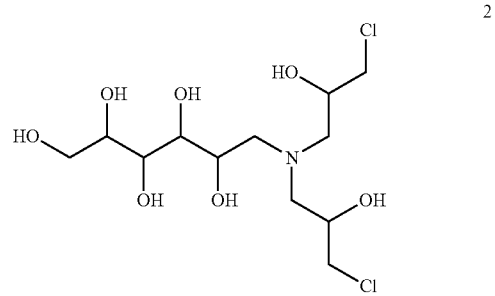 [SMILES: OCC(O)C(O)C(O)C(O)CN(CC(O)CCl)CC(O)CCl]

in an organic solvent;

e) admixing the solutions of steps c) and d) to obtain a solution comprising a compound of formula 3

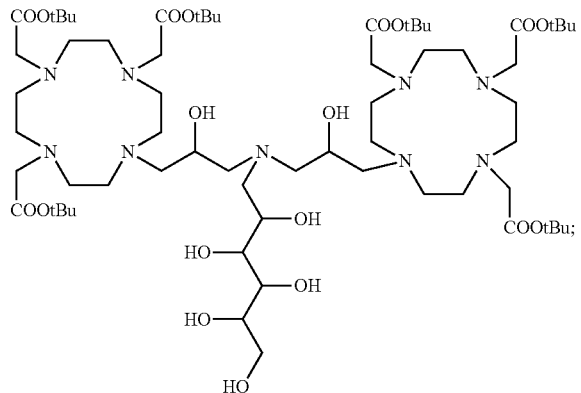

f) without isolating the compound from the solution of step e), removing the tert-butyl protecting groups from the compound of formula 3 to obtain a solution comprising a respective free ligand of formula 4

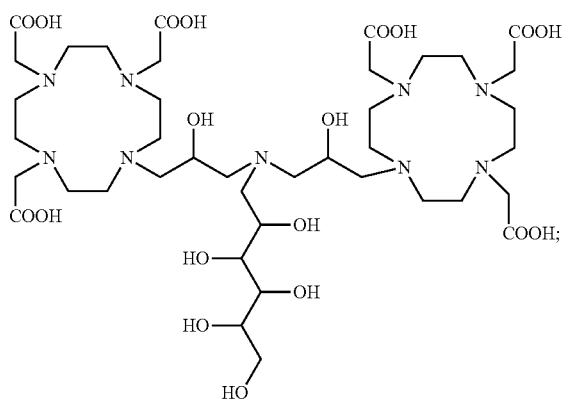

g) without isolating the free ligand of formula 4, adding gadolinium metal ions to the solution of step f) to obtain a solution comprising the respective dimeric complex of formula 5; and h) isolating the dimeric complex.

In a preferred aspect of the invention, the reaction solvent in all the steps following the preparation of the compound of formula 3 is an aqueous solvent or an aqueous solvent mixture. The aqueous solvent or aqueous solvent mixture advantageously does not comprise harsh materials such as TFA, TIPS and/or DCM.

Steps a) to c) of the process of the invention generally comprise the preparation of a solution comprising DO3A tri-tert-butyl ester 1A. In particular, the organic solution comprising 1A is prepared by converting the respective protected DO3A salt 1B to the protected DO3A 1A by using two immiscible solvents, as explained in detail below.

Step d) of the process of the invention comprises the preparation of the compound of formula 2, which may be obtained by alkylation of D-glucamine with epichlorohydrin. The alkylation is carried out in organic solvent, such as a dipolar organic solvent or in an aqueous mixture thereof. Suitable organic solvents for instance include DMAC, DMF, alcohols such as MeOH, and their mixtures. More preferably, the organic solvent is DMAC. The distillation of any aqueous solvent and/or epichlorohydrin excess from the mixture leads then to achieve a solution comprising the compound of formula 2 in the organic solvent which is suitable for use as such in the next step of the process, without isolation and/or further purification of the alkylation product.

The step e) of the process of the invention comprises the condensation (or coupling, as herein used interchangeably) of the intermediate compound of formula 2 with the DO3A tri-tert-butyl ester 1A, with the formation of the protected ligand of formula 3. The condensation reaction is preferably carried out in the presence of a base, e.g. acting as an acceptor of the formed HCl. Suitable bases for instance include anion exchange resins such as Amberlite GC 400, NMM, tBuOK, $Et_3N$, and DIPEA, wherein $Et_3N$ and DIPEA are preferred and DIPEA is particularly preferred.

In one embodiment, the condensation reaction is carried out by addition of the base and the organic solution comprising DO3A tri-tert-butyl ester 1A directly collected from step c) to the solution comprising the compound 2 collected from step d), to give an organic crude solution comprising the condensation product of formula 3 in an organic solvent mixture. Then, a purification of the organic crude leading to obtain the purified product in a water/organic solvent mixture, and the optional and preferred final distillation of any organic solvent allow to achieve the protected ligand of formula 3 in an aqueous solvent or an aqueous solvent mixture which can be used as such in the next step of the process, without isolation and/or further purification of the protected ligand itself.

Step f) of the process of the invention substantially comprises the removal of the carboxylic acids protecting groups from the protected ligand of formula 3 to give an aqueous solution or an aqueous mixture comprising the respective free ligand of formula 4. The deprotection by hydrolysis of tert-butyl protecting groups can be carried out in both acidic and basic conditions, by using reactants and conditions known to those skilled in the relevant art. In one embodiment, the deprotection is carried out by acidification of the aqueous solution or aqueous mixture comprising the protected ligand directly collected from step e) of the process, to achieve an acidic solution comprising the free ligand of formula 4. The acidification is preferably carried out by addition of an acid, for instance selected from HCl, $H_2SO_4$, and $H_3PO_4$. In a preferred embodiment the deprotection is performed by using HCl. Then, the neutralization of the acidic solution, subsequent purification and partial concentration of the resulting mixture lead to collect an aqueous solution or aqueous mixture comprising the ligand 4, that is used as such in the complexation step, without isolation.

Step g) of the process of the invention comprises the complexation of the ligand with gadolinium metal ions, to obtain the desired dimeric complex 5. The complexation reaction can conveniently be carried out according to know procedures, for instance by stoichiometric addition of a suitable Gd(III) derivative, particularly an oxide such as $Gd_2O_3$ or of a gadolinium salt to the solution comprising the ligand. In one embodiment the complexation reaction is carried out by addition of $GdCl_3$ to the solution comprising the ligand directly collected from step f) of the process. The resulting mixture is adjusted to a pH value of from about 5 to about 7 and maintained under stirring to give an aqueous solution or aqueous mixture comprising the gadolinium complex 5 that is then purified and concentrated to achieve solution comprising the desired dimeric complex 5 having the desired purity.

Step h) of the process of the invention comprises the final isolation of desired gadolinium complex 5. This step can conveniently be carried out according to know procedures. In one embodiment the solution comprising the purified complex collected from step g) is spray-dried to give the desired product as a white solid satisfying the required purity specifications.

Interestingly the process of the invention avoids or strongly reduces the use of harsh reagents, such as trifluoroacetic acid (TFA), and nasty solvents, such as dichloromethane, which are required and necessary in the process of the prior art and are difficult to handle when working on larger scales, for example on industrial processes.

Moreover, the process of the invention comprises steps that are carried out one-pot, which are suitable for a large-scale implementation, and which do not require the isolation of any of the prepared precursor (such as 1A) or intermediates. As a result, in addition to promote a reduction in process times, and of being easily implemented on larger scales as stated above, the process advantageously allows a significant increase in the overall process yield, from 10% (obtained with the process disclosed in WO2017098044) up to an overall yield of at least 20%, preferably of 25%, typically of about 28%, advantageously over 29%.

DETAILED DESCRIPTION OF THE INVENTION

In the present description, and unless otherwise provided, the term "intermediate" (e.g. used with reference to the compound of formula 2 deriving from the alkylation reaction of the D-glucamine with epichlorohydrin, or the protected ligand of formula 3) comprises within its meaning a molecule produced in the course of a chemical synthesis or preparation step of the process which is not itself the final product, but requires one (or more) further reactions e.g. alkylation/deprotection/complexation reaction(s) to give the final product of the process, namely the dimeric complex compound 5.

Unless otherwise provided, the term "precursor" (e.g. used with reference to the compound 1A) comprises within the meaning a molecule that participates in a chemical reaction promoting its transformation into another molecule, which includes or is derived from said precursor.

In the present description, the term "aqueous solvent" comprises within the meaning water and aqueous solutions, e.g. saline solutions, acting as a solvent. The aqueous solutions possibly including small amounts of organic solvents miscible with water, such as a volume percentage of 10% or lower of organic solvents miscible with water, preferably 8% or lower, and more preferably 5% or lower. Preferably the aqueous solvent is water.

The expression "water/organic solvent mixture" or, more simply, "aqueous solvent mixture" as used herein interchangeably, comprises within the meaning a mixture comprising two or more solvents which comprises an aqueous solvent, such as a mixture comprising water and one or more organic solvents all miscible with each other, to give a homogeneous solvent mixture, wherein the volume percentage of the one or more organic solvents is higher than 10%, preferably higher than 15%, more preferably higher than 20%. Suitable examples include mixtures of water and acetonitrile (or water/MeCN) used as eluents in the chromatographic purifications e.g. of the compound of formula 3, or the mixture comprising water/MeCN/DMAC e.g. resulting after dilution with water of the crude mixture resulting from the condensation reaction of step e). According to a preferred aspect of the present invention, the one or more organic solvents within the aqueous solvent mixture (as well as within the aqueous solvent, when present) is not a harsh solvent or material; indeed, the aqueous solvent mixture preferably does not comprise harsh solvents or materials such as TFA, TIPS and/or DCM.

Likewise, the expressions "aqueous solution" and "aqueous mixture" include in their meaning, respectively, a solution or a mixture containing water. Suitable examples include, respectively, a solution comprising one or more compounds, e.g. a reagent, an acid, a base or a reaction product in water (more in general, in an aqueous mixture), and a mixture, such as the water/organic mixture resulting from the addition of water or an aqueous solution to a reaction mixture in an organic solvent or solvent mixture. For example, the term "basic aqueous solution" refers to a solution comprising at least a base.

According to the present description, unless otherwise provided, the term "heterogeneous mixture" refers to a biphasic heterogeneous liquid mixture, i.e. a mixture comprising two liquids that are immiscible between each other.

In the present description the term "protecting group" (e.g. used with reference to the compound of formula 3) designates a protective group adapted for preserving the function of the group to which it is bound. Specifically, protective groups are used to preserve carboxyl functions. More specifically the term designates tert-butyl groups preserving the chelating function of carboxyl groups of the ligand by formation of tert-butyl esters [see, for a general reference on protecting groups and deprotecting conditions, T. W. Green and P. G. M. Wuts; *Protective Groups in Organic Synthesis*, Wiley, N.Y. 1999, third edition].

An embodiment of the invention relates to a process for the manufacturing of the dimeric compound 5 essentially as schematized in the following general synthetic Scheme 2:

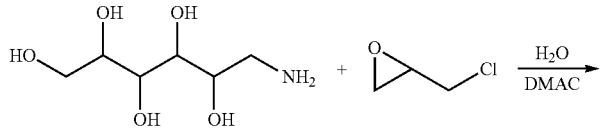

-continued
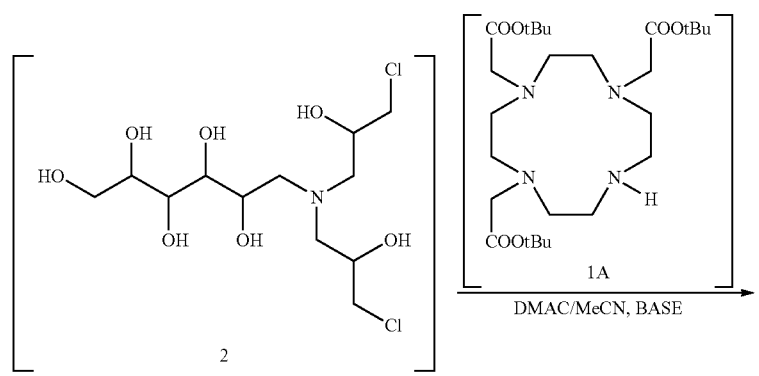
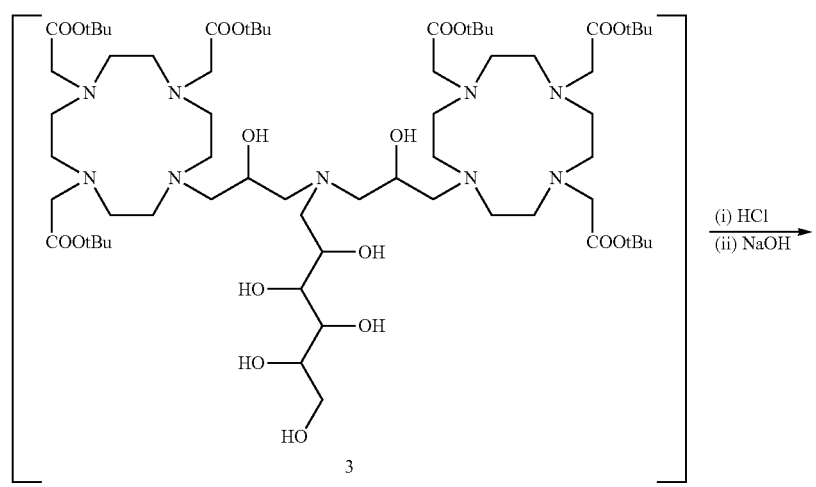
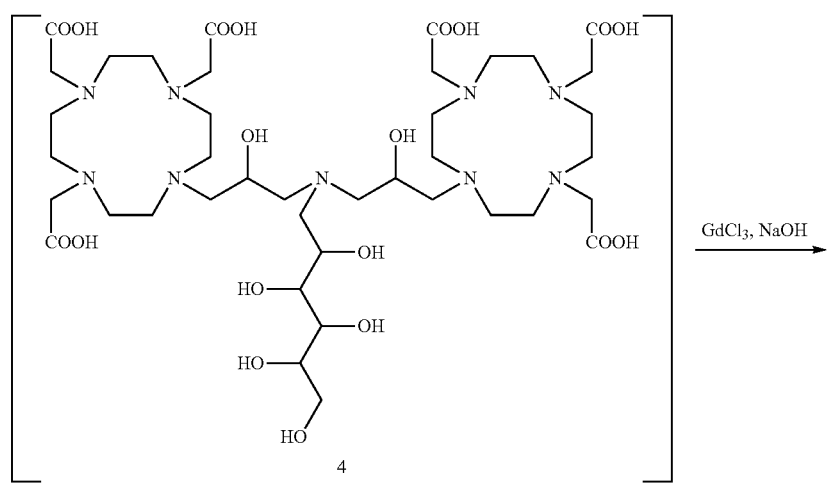

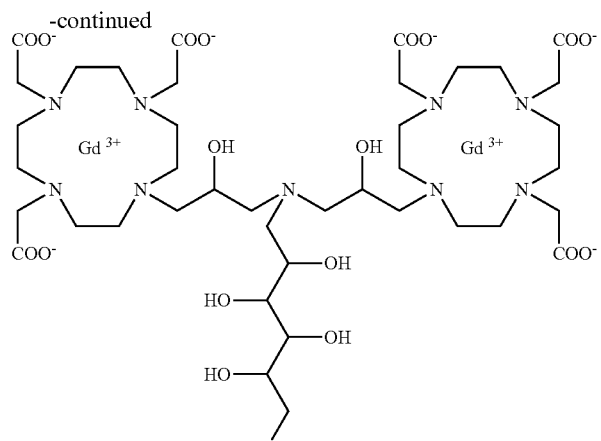

which comprises, as main steps:
a)-c) converting the salt of the DO3A tri-tert-butyl ester 1B to DO3A tri-tert-butyl ester 1A using a biphasic heterogeneous mixture, then collecting the organic phase thereby providing an organic solution comprising DO3A tri-tert-butyl ester 1A in the organic solvent;
d) reacting D-glucamine with epichlorohydrin to obtain a solution comprising the compound of formula 2 possibly in the presence of an organic solvent such as DMAC; and, without isolation of the product
e) reacting the compound of formula 2 from step d) with DO3A tri-tert-butyl ester 1A from step c) in the presence of a base and optional concentration of the solution to give an organic crude, dilution of the organic crude with water, a water/organic solvent mixture and/or an optional aqueous solution to obtain a water/organic crude, purification of the water/organic crude and optional removal of any organic solvent to give an aqueous solution or an aqueous mixture comprising the protected ligand of formula 3; and, without isolation of the product
f) acidifying the solution comprising the protected ligand of formula 3 from step e) to give an acidic aqueous solution or aqueous mixture comprising the respective deprotected ligand 4, neutralizing the acidic solution and purifying the resulting neutral solution to give an aqueous solution or aqueous mixture comprising the deprotected ligand 4, and, without isolation of the latter, g) adding gadolinium metal ions to the solution comprising the ligand 4 to obtain a solution comprising the corresponding complex compound 5; and
h) isolating the complex.

Step a)

Step a) provides for obtaining a heterogeneous mixture that comprises the salt 1B. Indeed, it has been found that it is possible to decrease the reaction times of the conversion step b) by using such a heterogeneous mixture.

In particular, step a) provides for admixing the salt 1B with a basic aqueous solution and an organic solvent immiscible with the basic aqueous solution, whereby the two immiscible liquids (the basic aqueous solution and the organic solvent immiscible with the basic aqueous solution) form the heterogeneous mixture. The heterogeneous mixture thus comprises both the basic aqueous solution and the organic solvent, as well as the salt 1B.

The salt 1B has the following formula

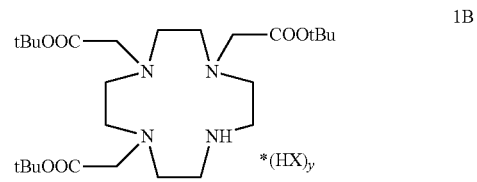

wherein X is a halogen anion, and y is an integer from 1 to 3. According to a preferred embodiment, y is 1, and/or X is bromide (Br⁻). According to a more preferred embodiment, y is 1 and X is bromide (Br⁻), so that the salt 1B is DO3A 3t-Bu-HBr.

The salt 1B can be obtained according to known methods. For example, the salt 1B can be advantageously obtained by carrying out the following steps:
I) reacting cyclen (1,4,7,10-tetraazacyclododecane) with an acetic ester of formula XCH$_2$OOtBu, wherein X is as defined above, in an organic solvent and in the presence of an auxiliary base, to provide a mixture;
II) adding water to the mixture of step I), preferably in an amount of 2.5 to 10 times w/w with respect to the amount of cyclen of step I), to obtain a suspension comprising the salt 1B; and
III) collecting and washing the salt 1B;
as disclosed in more details in WO2021116165.

According to a preferred embodiment, the organic solvent immiscible with the basic aqueous solution is an ether, such as methyl tert-butyl ether (MTBE). These ethers, which are immiscible with the basic aqueous solution, have been found particularly effective for converting the salt 1B in the conversion step b).

According to a preferred embodiment, the amount of organic solvent in step a) is 1.0 to 5.0 w/w, preferably is 1.2 to 3.0 w/w, more preferably is 1.4 to 1.6 w/w, and even more preferably is 1.5 w/w, with respect to the amount of salt 1B.

The basic aqueous solution comprises a base, which is preferably an inorganic base, such as an inorganic base selected from the group consisting of KOH, NaOH, Na$_2$CO$_3$, and K$_2$CO$_3$. Such base can preferably be in a molar ratio of 1.0 to 4.0 mol, preferably of 1.2 to 3.0 mol, more preferably of 1.7 to 2.3 mol, and even more preferably is 2.0 mol, with respect to 1 mol of salt 1B. These molar ratios have been found to be particularly effective for converting the salt 1B in the conversion step b), in particular when the salt 1B has y=1. When the salt 1B has y=2 or 3, the amount of basic aqueous solution is preferably higher than the one stated above, and in particular is preferably 2-times or 3-times (respectively) higher than the amount disclosed above when y is 1.

According to a preferred embodiment, the amount of basic aqueous solution in step a) is 2.0 to 10 w/w, preferably is 2.2 to 6.0 w/w, more preferably is 2.8 to 3.2 w/w, and even more preferably is 3.0 w/w, with respect to the amount of salt 1B.

The heterogeneous mixture provided in step a) is used as is (i.e., without isolating the salt 1B from the heterogeneous mixture) in the following conversion step b).

Step b)

Step b) provides for converting the salt 1B to DO3A tri-tert-butyl ester 1A.

In particular, during step b), the salt 1B is converted due to the basic conditions of the basic aqueous solution to its correspondent DO3A tri-tert-butyl ester 1A. As DO3A tri-tert-butyl ester 1A is more soluble in the organic solvent than in the basic aqueous solution, the converted DO3A tri-tert-butyl ester 1A can be found solubilized within the organic solvent.

Step b) is a reaction that occurs in a heterogeneous (two-phase) medium, and thus it is preferably carried out by stirring the heterogenous mixture obtained by step a) to increase the interactions between the two phases, preferably for a time under 5 hours, more preferably for a time of 1 to 5 hours, even more preferably for a time of 1.5 to 3 hours, and most preferably for a time of 2 hours.

According to an embodiment, step b) is carried out by adjusting and/or maintaining the temperature in the range of 15 to 50° C., preferably of 20 to 30° C., more preferably of 23 to 27° C., and even more preferably to 25° C., for example while stirring and for a time as disclosed above.

The heterogeneous mixture comprising DO3A tri-tert-butyl ester 1A as obtained by step b) is advantageously used as is in the next step c).

Step c)

Step c) provides for collecting the organic solvent from the heterogeneous mixture of the previous step b). As stated above, DO3A tri-tert-butyl ester 1A can be found solubilized within the organic solvent, whereby collecting the organic solvent amounts to obtaining an organic solution comprising DO3A tri-tert-butyl ester 1A.

This collection step c) can be carried out according to known methods, for example by discarding the basic aqueous solvent from the heterogeneous mixture.

After step c) and before step e), the organic solution comprising DO3A tri-tert-butyl ester 1A can be subjected to a solvent changing step, whereby the solvent thereof is changed to another organic solvent that has been found to be more suitable and efficient for the condensation step e). In particular, after step c) and before step e), the organic solution comprising DO3A tri-tert-butyl ester 1A is preferably subjected to a solvent changing step to obtain an organic solution comprising DO3A tri-tert-butyl ester 1A wherein the organic solvent comprises MeCN or a $C_2$-$C_4$ alcohol, preferably isopropanol. According to a preferred embodiment, when the organic solution is an ether, such as MTBE, the solvent changing step comprises the steps of (i) adding a MeCN or a $C_2$-$C_4$ alcohol, preferably isopropanol, to the organic solution, and (ii) removing the ether from the organic solution by distillation, whereby the organic solvent of the organic solution comprising DO3A tri-tert-butyl ester 1A comprises MeCN or a $C_2$-$C_4$ alcohol, preferably isopropanol. When the solvent changing step is carried out by adding a $C_2$-$C_4$ alcohol, preferably isopropanol, such alcohol is preferably added in an amount of preferably 0.4 to 0.8 w/w, more preferably of 0.5 to 0.7 w/w, with respect to the amount of DO3A tri-tert-butyl ester 1A.

After step c) and before step e), for example after the solvent changing step disclosed above, the organic solution comprising DO3A tri-tert-butyl ester 1A preferably has a concentration of 40 to 80% w/w, preferably of 50 to 70% w/w, more preferably of 56 to 63% w/w. Such a concentration can be obtained for example by conventional means, for example by concentrating the organic solution e.g. by evaporating the solvent. The range of concentration above has been found to improve the conjugation reaction of step e).

Step d)

This step comprises preparing a solution comprising the intermediate compound of formula 2 by reacting D-glucamine with epichlorohydrin. In one embodiment the reaction is carried out in a mixture of solvents, preferably in water/DMAC, by using a slight excess of epichlorohydrin over the stoichiometric amount, for example of from 2 to 3 and more preferably of about 2.2 moles of epichlorohydrin per mole of D-glucamine. Preferably, the reaction of step d) is carried by using a slight excess of epichlorohydrin over the stoichiometric amount, for example from 2 to 3 moles, more preferably from 2.05 to 2.5 moles, and even more preferably about 2.2 moles of epichlorohydrin per mole of D-glucamine.

In a preferred embodiment, step d) of the process of the invention comprises:

d1) adding an aqueous solution comprising D-glucamine to a solution comprising epichlorohydrin in DMAC to give the intermediate compound of formula 2 in a water/DMAC solvent mixture; and d2) removing the water from the solvent mixture, to obtain a solution comprising the compound of formula 2 in the organic solvent.

The addition of D-glucamine to the solution comprising epichlorohydrin is preferably carried out at room temperature, in a time of about 2 h, to give a mixture that is kept under stirring at a temperature of from 15 to 30° C., preferably from 15 to 25° C. and more preferably from 20 to 25° C., for a time of from 16 to 24 h, preferably from 16 to 20 h and more preferably of about 17 h.

The mixture is then distilled, to remove water and any optional epichlorohydrin residue. The distillation is preferably carried out at reduced pressure, and a temperature preferably of 40-65° C., leading to achieve a solution comprising the desired intermediate compound of formula 2 in DMAC with a residual water content preferably <2% w/w. The achieved solution is then used as such in the subsequent condensation reaction, without requiring any isolation or purification of the product.

Step d) and steps a) to c) can be carried out in parallel, or in any possible order (e.g. steps a) to c) first and then step d), or step d) first and then steps a) to c)).

Step e)

This step essentially comprises the condensation of the DO3A tri-tert-butyl ester 1A with the intermediate 2, in the presence of a base such as $Et_3N$ or, more preferably, DIPEA. The condensation is preferably carried out by admixing the base and the solutions of the ester 1A in MeCN or a $C_2$-$C_4$ alcohol, such as isopropanol, collected from step c) with the solution comprising the intermediate 2 in DMAC directly collected from step d) to give a raw solution (or crude)

comprising the protected ligand of formula 3 in the mixture of the MeCN/DMAC or alcohol/DMAC organic solvents that is then purified.

In one embodiment, the organic crude solution resulting from the condensation reaction is diluted with water or is partially concentrated and then diluted with water or an aqueous solvent mixture, preferably water/MeCN, to obtain a water/organic crude, or aqueous crude, as herein used interchangeably.

In a preferred embodiment, the water/organic crude thus obtained or, preferably, the organic crude resulting from the condensation reaction are added with an aqueous solution which promotes the precipitation of reaction salts, including DO3A tri-tert-butyl ester hydrochloride, which are then removed by filtration, to provide a water/organic filtered solution. The water/organic crude or the water/organic filtered solution are then purified, preferably by chromatography.

In one embodiment, the aqueous solution used to promote the precipitation of the hydrochloride salts is aqueous ammonia.

More particularly, step e) of the process preferably comprises:
- e1) condensation of the intermediate compound of formula 2 from step d) with DO3A tri-tert-butyl ester 1A from step c) in the presence of a base, preferably DIPEA, to give an organic crude solution comprising the condensation product of formula 3 and reaction salts in the organic solvent mixture, and optional concentration of the organic crude;
- e2) dilution of the organic crude of step e1) with water or a water/organic solvent mixture, preferably water/MeCN, to give a water/organic crude;
- e3) optional addition to the water/organic crude of an aqueous solution promoting the precipitation of reaction salts that are removed by filtration to give a water/organic filtered solution; or
- e4) dilution of the organic crude of step e1) with the aqueous solution promoting the precipitation of reaction salts that are removed by filtration, to give a water/organic filtered solution;
- e5) purification of the water/organic crude of step e2), or of the water/organic filtered solution of steps e3) or e4), to give a solution comprising the protected ligand of formula 3 in a water/organic solvent mixture that can be used in the next deprotection step of the process without requiring any isolation or further purification of the protected product; and
- e6) optional removal of any organic solvent from the mixture, to obtain a solution comprising the protected ligand of formula 3 in water that is used in the next deprotection step of the process without requiring any isolation or further purification of the protected product.

The condensation reaction is preferably carried out by addition of the base and a solution comprising the ester 1A in MeCN or in a $C_2$-$C_4$ alcohol, such as in isopropanol collected from step c) of the process to the solution comprising the intermediate compound of formula 2 in DMAC collected from step d).

Suitable amounts of base and ester 1A are conveniently determined with respect to the amount of D-glucamine subjected to the reaction. In one embodiment, the condensation reaction is carried out by using from 1.6 to 2.4 moles and preferably about 1.8 moles of ester 1A, and from 2 to 4 moles, preferably about 2.3 moles of DIPEA per mole of starting D-glucamine subjected to reaction.

The addition is preferably performed at a temperature of 40-50° C. The condensation reaction is then carried out at a temperature of from 50 to 80° C., preferably from 65 to 75° C. for a time e.g. of 60-80 h, preferably of 70-75 h, to give a raw solution comprising the desired condensation product of formula 3 and hydrochloride salts in a MeCN/DMAC or alcohol/DMAC solvent mixture.

In one embodiment, the raw solution is then diluted with water to give a water/organic crude having, preferably, a concentration of about 25-30%, more preferably of about 25% (w/w). In one preferred embodiment, the aqueous crude comprises an amount of water which by weight is at least equal to the amount of the organic solvent, specifically MeCN in the mixture; more preferably the crude has a water:MeCN ratio of about 60:40.

The water/organic crude is then purified, preferably by chromatography, more preferably on resins, even more preferably on adsorbent resins, such as Amberlite XAD® 1600. In a preferred embodiment, the aqueous crude is purified on an adsorbent resin, such as Amberlite XAD® 1600, by using a water/MeCN mixture as eluent, allowing to achieve both the unreacted DO3A tri-tert-butyl ester 1A and the pure condensation product as separated fractions in a water/MeCN solvent mixture.

In another embodiment the raw solution resulting from the condensation reaction is first concentrated by removing at least a part of the MeCN, e.g. by distillation. The concentrated solution is then diluted with water or with a mixture of water:MeCN allowing to obtain a water/organic crude having the above water:MeCN ratio, that is then purified by chromatography, as above said.

When the raw solution resulting from the condensation reaction comprises alcohol/DMAC as solvent mixture, the alcohol is removed (e.g. by distillation), and then the resulting solution is diluted with water or with a mixture of water:MeCN allowing to obtain a water/organic crude having the above water:MeCN ratio, that is then purified by chromatography, as above said.

Optionally, the water/organic crude obtained as above said is added with an aqueous solution such as aqueous ammonia which promotes, by cooling of the mixture, the precipitation of the unreacted DO3A tri-tert-butyl ester as hydrochloride, that is then removed by filtration and, optionally recycled. The filtered solution devoid of most of the chloride salts is then purified by chromatography on an adsorbent resin, such as Amberlite XAD® 1600 resin as above said, to give the residual DO3A tri-tert-butyl ester 1A and the pure condensation product as separated fractions in a water/organic, such as a water/MeCN solvent mixture.

In a preferred embodiment, the aqueous solution, e.g. including aqueous ammonia is added directly into the organic raw solution resulting from the condensation reaction promoting, by cooling of the mixture, the precipitation of the unreacted DO3A tri-tert-butyl ester as hydrochloride that is then removed by filtration and, optionally recycled. The filtrate devoid of most of the chloride salts is then purified by chromatography on an adsorbent resin, such as Amberlite XAD® 1600 resin as above said, to give the residual DO3A tri-tert-butyl ester 1A and the pure condensation product as separated fractions in a water/organic, such as a water/MeCN, solvent mixture.

The optional final distillation of the organic solvent, e.g. under reduced pressure, from pure fractions leads then to achieve the condensation product of formula 3 in an aqueous solution with a final concentration of 5-15% (w/w), preferably of about 10% (w/w), that is suitable for use in the subsequent deprotection step as such, without requiring any isolation or additional purification of the intermediate.

Interestingly, the above procedural steps allow to obtain the protected condensation product 3 in an aqueous solvent or aqueous solvent mixtures, thus making it possible to carry out its deprotection and complexation to the final complex 5 by using water, and more in general aqueous solvents or aqueous solvent mixtures, as the only or one of the main reaction solvents. The protected condensation product 3 in an aqueous solvent can be obtained according to various methods known to the skilled person. For example, as stated above, the organic crude solution comprising compound of formula 3, e.g. obtained by reacting the compound of formula 2 from step d) with DO3A tri-tert-butyl ester 1A from step c), can be diluted with water, a water/organic solvent mixture, or an aqueous solution, thus obtaining a water/organic crude. Before removal of the organic solvent, the water/organic crude can be purified via chromatography, preferably via a resin, and more preferably via an adsorbent resin, such as Amberlite XAD® 1600. Then, the organic solvent can be removed to obtain the aqueous solution comprising the compound of formula 3, for example by distillation e.g. under reduced pressure. Also the protected condensation product 3 in an aqueous solvent mixture can be achieved according to various methods known to the skilled person. For example, the organic crude solution comprising compound of formula 3, e.g. obtained by reacting the compound of formula 2 from step d) with DO3A tri-tert-butyl ester 1A from step c), can be diluted with water, a water/organic solvent mixture, or an aqueous solution, thus obtaining a water/organic solution to be used in the subsequent steps without isolation of the product 3.

Therefore, according to a preferred aspect of the present invention, the present invention comprises the further step of converting the solution comprising a compound of formula 3 to an aqueous solution comprising, or to an aqueous mixture comprising, a compound of formula 3. Preferably, this further step is carried out by: (i) diluting the solution comprising a compound of formula 3 with water, a water/organic solvent mixture, or an aqueous solution, thus obtaining an aqueous mixture (or a water/organic solution), and (ii) optionally removing the organic solvent, e.g. by distillation, thus obtaining an aqueous solution.

Step f)

This step comprises the deprotection of the protected ligand of formula 3 by removing carboxyl protecting groups leading to achieve an aqueous solution or aqueous mixture comprising the respective free ligand 4. The reaction is preferably carried out by acidification of the aqueous solution or mixture comprising protected ligand of formula 3 directly collected from step e) of the process.

In one embodiment the step f) of the process comprises:
 f1) Addition of an acid to the aqueous solution or aqueous mixture comprising the compound of formula 3 collected from step e) to achieve acidic solution comprising the free ligand 4;
 f2) Addition of a base to the acidic solution, to achieve a substantially neutralized solution comprising the ligand 4;
 f3) Purification of the neutralized solution and subsequent optional concentration, to give an aqueous solution or aqueous mixture comprising the free ligand 4 that is suitable for use as such in the next complexation reaction, without requiring any isolation of the ligand.

In one embodiment, the solution comprising the protected compound of formula 3 is acidified by addition of an acid, such as 34% aqueous HCl. The acidification is performed by using a large excess of HCl, e.g. from 30 to 100, preferably from 30 to 80, and, more preferably, of 40-50 times the molar amount of the protected compound 3.

The addition of the acid is carried out at a temperature of 20-35° C., preferably of 30-35° C. The resulting solution is then maintained under stirring at 30-40° C. for from a time of from 10 to 36 h, preferably for 25-30 h, by following the deprotection of the ligand e.g. by chromatography.

The acidic solution is then cooled e.g. at 25° C., and then is neutralized by addition of a base, preferably NaOH, to achieve a raw solution with a final pH of from 6.5 to 7.5 which is then purified.

The purification steps preferably include: i) distillation of the neutralized solution, to remove the formed t-butanol, ii) desalination of the distillation residue, and iii) chromatographic purification of the desalinated solution.

In particular, in one embodiment, the solution resulting from the addition of a base is first distilled, preferably at a temperature of from 40 to 60° C. to remove formed t-butanol. The distillation residue is then desalinated, preferably by nanofiltration, and the collected solution is purified.

In one embodiment, the solution obtained by nanofiltration is first concentrated, for instance under vacuum at a temperature e.g. of 40 to 60° C., preferably of about 50° C., to a concentration preferably of 23-27% (w/w) and then is purified by elution on resins, more preferably on Amberlite XAD® 1600. The eluate is optionally treated with an activated carbon, such as Carbopuron 4N, and concentrated under vacuum at about 50° C. to achieve an aqueous solution or aqueous mixture comprising the ligand of formula 4 with final concentration preferably ranging from 8-25%, that is used as such in the next complexation reaction, without any isolation of the ligand.

Advantageously, the above procedure comprises using water as the sole or one of the main reaction solvent, thus avoiding or reducing the use of organic solvents, and in particular of harsh solvents, such as DCM, and of harsh reactant, such as TFA and TIPS, which are required in the process of above-mentioned prior art. These harsh materials are difficult to handle, and are thus unsuitable for use in large-scale productions. Moreover, this step leads to achieve the desired ligand in an aqueous solution or aqueous mixture ready for use in the complexation reaction, without requiring its isolation.

Step g)

This step comprises the complexation of the dimeric ligand of formula 4 with gadolinium ions to achieve an aqueous solution or aqueous mixture comprising the desired chelated complex 5.

More particularly, the step preferably comprises:
 g1) Addition of a gadolinium salt, such as $GdCl_3$ to the solution comprising the ligand collected from step f) to obtain a mixture comprising the dimeric chelated complex 5;
 g2) Addition of a base to give a mixture with a pH value of from about 5 to about 7;
 g3) Purification of the mixture, to give a solution comprising the dimeric complex of formula 5; and
 g4) Concentration of the collected solution.

The reaction is preferably carried out by addition of $GdCl_3$ directly to the solution comprising the ligand collected from the previous step of the process. The addition is preferably performed at a temperature of 25-45° C. The required amount of $GdCl_3$ leading to achieve the exhaustive complexation of the ligand is determined by titration of the ligand solution, for instance by using copper sulfate as titrating agent, according to know procedures.

In one embodiment, the ratio between ligand of formula 4 and added $GdCl_3$ is from 1:1.98 to 1:2.02 (mol/mol); more preferably is of 1:2.00 to ensure the exhaustive consumption of the added lanthanide ion.

After the addition, the pH of the resulting mixture is adjusted to a value ranging from about 5 to about 7.5 by addition of a base, preferably NaOH.

For instance, in one embodiment $GdCl_3$ is added to the ligand solution e.g. at a temperature of 20-25° C. The resulting mixture is adjusted to a pH value of 7-7.5, such as about 7 by addition of NaOH, and then is maintained under stirring at 20-25° C. for about 25 h, thus achieving an exhaustive complexation of the ligand.

In one alternative embodiment, $GdCl_3$ and the necessary amount of NaOH maintaining the pH at the desired neutral value can be added simultaneously, and the achieved mixture is then maintained under stirring for about 25 h, as above said.

In a preferred embodiment, the mixture resulting from the addition of $GdCl_3$ is adjusted to a pH value from about 5 to about 6, preferably from 5 to 5.6, more preferably of about 5.3, and then is maintained under stirring at about 40° C. for 1-4 h, e.g. about 2 h. The optional presence of residual free species such as free $Gd^{3+}$, ligand or partially complexed ligand is then assessed, e.g. by titration and/or HPLC methods, and compensated by addition of calculated amounts of ligand or $GdCl_3$ to give an aqueous solution or aqueous mixture comprising the dimeric complex of formula 5 which is then purified.

The purification is preferably carried out by chromatography, preferably on resins.

In one embodiment the purification comprises the elution of the mixture resulting from the complexation reaction on a polymeric resin, preferably a Amberlite XAD® 1600 resins.

In another embodiment, the purification comprises a first elution of the mixture resulting from the complexation reaction on a chelating resin, for instance selected from Hi Trap IMAC FF, Lewatit MonoPlus TP 260, Lewatit TP 208, IRC748I, DIAION CR11, SiliaMets AMPA and SiliaMets DOTA, and preferably from Diaion CR11 and Amberlite IRC748, allowing to minimize any optional free gadolinium content, and the additional purification of the collected eluate on a polymeric resin, such as a Amberlite XAD® 1600 resin.

According to a practical implementation, a mixture adjusted to an about neutral pH value is properly purified by elution on Amberlite XAD® 1600 resin.

The mixtures resulting from regulation of the solution pH to lower values, such as 5-5.6, are otherwise preferably eluted first on a chelating resin such as the Amberlite IRC748 or the Diaion CR11 resin. The collected eluates are then preferably re-adjusted to a pH value of about 5.5-6 and concentrated, preferably under vacuum at 50° C. to obtain an aqueous solution or aqueous mixture comprising the dimeric complex with a concentration preferably of about 25% (w/w) that is then purified on Amberlite XAD® 1600 resin.

Collected fractions are then optionally treated with charcoal and filtered. The resulting filtered solution is then preferably concentrated, for instance by distillation under vacuum at 45-55° C. to give a solution comprising the dimeric complex 5 with a final concentration of about 25% (w/w).

Step h)

The dimeric complex of formula 5 is then isolated according to step h). The complex can be isolated from the aqueous solution or aqueous mixture from step g) for instance by lyophilization or by spray-drying. In one preferred embodiment the desired dimeric complex is obtained as a white solid by spray-drying the solution directly collected from step g) of the process.

The overall yield of the process, determined from the limiting reactant as DO3A tri-tert-butyl ester 1A, is of at least 20%, preferably of 25%, more preferably of about 28%, or even >29%.

Interestingly the above process comprises steps that are carried out one-pot, which are suitable for a large-scale implementation, and which do not require the isolation of any of the prepared precursor (such as the compound of formula 1A) or reaction intermediates. As a result, the synthetic approach object of the present invention allows to achieve the final product with an overall yield increased of at least about 18% over the process disclosed in WO2017098044.

In addition, the lack of intermediates isolation allows for a reduction of the overall time process.

Moreover, the proposed process comprises the use of water, or more in general of aqueous solvent or aqueous solvent mixture, as the reaction solvent in all the steps following the preparation of the coupling product 3. In particular, when the compound of formula 3 is prepared in step e) in an organic solvent, e.g. when it is prepared by reacting the compound of formula 2 from step d) with DO3A tri-tert-butyl ester 1A from step c), the organic solvent can be replaced with an aqueous one or with an aqueous mixture by methods known to the skilled person, e.g. by first diluting with water, a water/organic solvent mixture, or an aqueous solution the organic solution comprising the compound of formula 3, and then optionally by removing the organic solvent to obtain an aqueous solution comprising the compound of formula 3.

Using aqueous solvents or aqueous solvent mixtures as reaction solvent in all steps following the preparation of the coupling is very advantageous, particularly from the standpoint of costs, environmental impact, and ease of implementation in industrial scale. Indeed, the process disclosed in WO2017/098044 employs solvents such as DCM and materials such as TFA and TIPS that, beside being expensive, are also difficult to handle, particularly when scaling the process on an industrial scale. These solvents and materials might also not be safe for the health of workers. On the contrary, the process of the invention avoids or strongly reduces the use of organic solvents by using aqueous solvents or aqueous solvent mixtures in all the steps following the preparation of the compound of formula 3, thus being suitable, and easily implementable, for working on larger scales, for example for working in industrial processes. Moreover, the process of the invention surprisingly provides very high yields of the isolated dimeric complex, in particular yields that are higher than the ones of the prior art process, even though it comprises using aqueous solvents or aqueous solvent mixtures following the preparation of the compound of formula 3. Furthermore, by employing a larger amount of aqueous solvent or aqueous solvent mixture, the process of the invention reduces the use of harsh solvents and materials, thus being more favourable from a cost, environmental and safe point of view compared to the process of the prior art.

All solvents and starting materials, including reactants such as epichlorohydrin, D-glucamine, and the hydrobromide salt of DO3A tri-tert-butyl ester are commercially available, or can be obtained according to know procedures.

In a preferred embodiment, the hydrobromide salt of the DO3A tri-tert-butyl ester used as starting material for the preparation of a solution comprising the respective ester 1A is prepared by using the manufacturing process described in the patent application WO2021/116165 (same applicant as the present application) and exemplified below, in the experimental section of the description, and stored until the use.

Non-limiting examples of preferred embodiments of the process of the invention are reported in the following section, aimed to illustrate the invention in greater detail without limiting its scope.

Experimental Part

Abbreviations and Definition of Terms

DO3A tri-tert-butyl ester
(DO3A tBu): tri-tert-butyl 1,4,7,10-tetraazacyclododecane-1,4,7-triacetate
DO3A tri-tert-butyl ester-HBr
(DO3A tBu-HBr): tri-tert-butyl 1,4,7,10-tetraazacyclododecane-1,4,7-triacetate hydrobromide salt
TAZA: 1,4,7,10-tetraazacyclododecane
tBuOK Potassium tert-butoxide
DMAC N,N-dimethylacetamide
DMC Dichloromethane
DMF Dimethyl formamide
DIPEA N,N-diisopropylethylamine
GdCl3 Gadolinium chloride
HCl Hydrocloric acid
KOH Potassium hydroxyde
ACN/MeCN Acetonitrile
NaOH Sodium hydroxyde
$Na_2CO_3$ Sodium carbonate
$NH_3$ Ammonia
MRI Magnetic Resonance Imaging
MeCN Acetonitrile
MTBE Methyl t-butyl ether
NMM N-methylmorpholine
$K_2CO_3$ Potassium carbonate
TFA Trifluorocetic acid
TIPS triisopropylsilane
FLD Fluorescence detector
UV/Vis Unltraviolet/Visible
HPLC Characterization of the Obtained Compounds.
General Procedures
Procedure 1: HPLC Characterization and Determination of the Assay of the DO3A-Tri-Tert-Butyl Ester
Chromatographic Conditions
  HPLC system Liquid chromatograph (e.g. Agilent 1100), equipped with solvent delivery system, autosampler, column thermostat, degasser and diode array detector or variable wavelength detector (or equivalent).
  Stationary phase: Zorbax Eclipse XDB-C8, 5 μm, 150× 4.6 mm
  Column temperature 45° C.
  Mobile phase: A: 0.01 M $K_2HPO_4$, 0.017 M $H_3PO_4$
    B: Acetonitrile

| Elution: Gradient | |
| --- | --- |
| Time (min) | % B |
| 0 | 5 |
| 30 | 80 |
| 35 | 80 |
| 38 | 5 |
| 45 | 5 |

Flow 1 mL/min

Temperature 45° C.

Detection UV, 210 nm, Bw=8 nm; Reference 360 nm, Bw=100 nm

Injection volume 10 μL

Stop time 35 min

Reference peak DO3A 3tBu

Retention time DO3A 3tBu≅14-15 min.

Procedure 2: HPLC Method for Monitoring the Formation of Intermediate 2

This method is employed for monitoring the mixture at the end of the alkylation of the D-glucamine and after distillation of the water.

Chromatographic Conditions
  HPLC system: Liquid chromatograph (e.g. Agilent 1100), equipped with solvent delivery system, autosampler, column thermostat, degasser and diode array detector or variable wavelength detector (or equivalent)
  Stationary phase: SeQuant ZIC-cHilic 3 μm, 150×2.1 mm (Merck P.N. 1.50658.0001)
  Column Temperature: 40° C.
  Mobile phase: gradient elution
    Eluent A=5 mM ammonium acetate
    Eluent B=ACN/MeOH, 75/25

| Elution: Gradient | |
| --- | --- |
| Time (min) | % B |
| 0 | 97 |
| 5 | 97 |
| 30 | 20 |
| 40 | 20 |
| 45 | 97 |
| 60 | 97 |

Flow rate: 0.25 mL/min

Detection: UV, 210-240 nm

Injection volume: 10 μL

Run time: 60 min

Dilution solution ACN/MeOH, 75/25

Sample preparation: add 200 μL of 5 mM ammonium acetate solution to 75 μL of mixture and dilute to 5 mL with dilution solution.

Procedure 3: HPLC Method for Monitoring the Formation and the Purification of Intermediate 3

General procedure

The method is used for monitoring the formation of the Intermediate 3 and the purification step.

Analytical Conditions
  HPLC system Liquid chromatograph Agilent 1100
  Stationary phase: Gemini, 5 μm, 250×4.6 mm (Phenomenex, item 00G-4435-EO)
  Column temperature 40° C.
  Mobile phase: A: mobile phase A
    B: MeCN

| Elution: Gradient | |
|---|---|
| Time (min) | % B |
| 0 | 40 |
| 5 | 40 |
| 30 | 90 |
| 35 | 90 |
| 36 | 40 |
| 45 | 40 |

Flow 0.7 mL/min
Detection UV/210 nm
Injection volume 10 μL
Stop time 45 min
INT 2 $R_t$ 21 min
Mobile phase A
Preparation of the Solution
  In a 1000 mL volumetric flask accurately weigh 2.0 g of ammonium acetate and then dilute to volume with water. In a 1000 mL volumetric flask transfer 600 mL of ammonium acetate solution and 300 mL of methanol. Sonicate for half an hour.
Procedure 4: HPLC Method for Monitoring the Formation and Purification of the Chelating Ligand 4.
General Procedure
  The monitoring of the formation and purification of the dimeric ligand 4 were performed by reverse-phase HPLC with UV detection at 210 nm.
Analytical Conditions
  HPLC system Liquid chromatograph Agilent 1260 Infinity
  Stationary phase: Synergi Polar-RP, 4 μm, 150×4.6 mm (Phenomenex, item 00F-4336-EO)
  Column temperature 40° C.
  Mobile phase: A: 10 mM $KH_2PO_4$
    B: Methanol

| Elution: Gradient | |
|---|---|
| Time (min) | % B |
| 0 | 0 |
| 5 | 0 |
| 35 | 60 |
| 40 | 60 |
| 41 | 80 |
| 46 | 80 |
| 47 | 0 |
| 60 | 0 |

Flow 0.8 mL/min
Detection UV/210 nm
Injection volume 10 μL
Stop time 60 min
Compound 4 $R_t$ 2.4 min Example 1: Synthesis of DO3A-Tri-Tert-Butyl Ester Hydrobromide Salt The synthesis of the starting DO3A tri-tert-butyl ester hydrobromide salt was performed by using the procedure disclosed in WO2021116165. In particular: to a suspension of commercially available TAZA (14.39 kg; 83.53 mol) and sodium acetate (21.58 kg; 263.12 mol) in DMAC (98.07 kg; 104.33 L), a solution of tert-butyl bromoacetate (51.32 kg; 263.12 mol) in DMAC (50.72 kg; 53.96 L) was added at 10° C. during 2.5 h. Then the temperature was raised to 25° C. and the mixture was stirred for 24 h at this temperature. Water (57.56 kg) was then added in 0.5 h and after 2 h the mixture was centrifuged and washed with water (2×57 kg). The wet solid was dried under vacuum obtaining 36.62 kg; 61.48 mol of DO3A tri-tert-butyl ester hydrobromide (73.6% yield). The assay determined by HPLC (against standard) of the product is 100% w/w; the assay determined by NMR (against standard) is 99.86% w/w.

Example 2: Preparation of the Dimeric Compound 5

The dimeric complex compound 5 is obtained by using the synthetic procedure schematized below

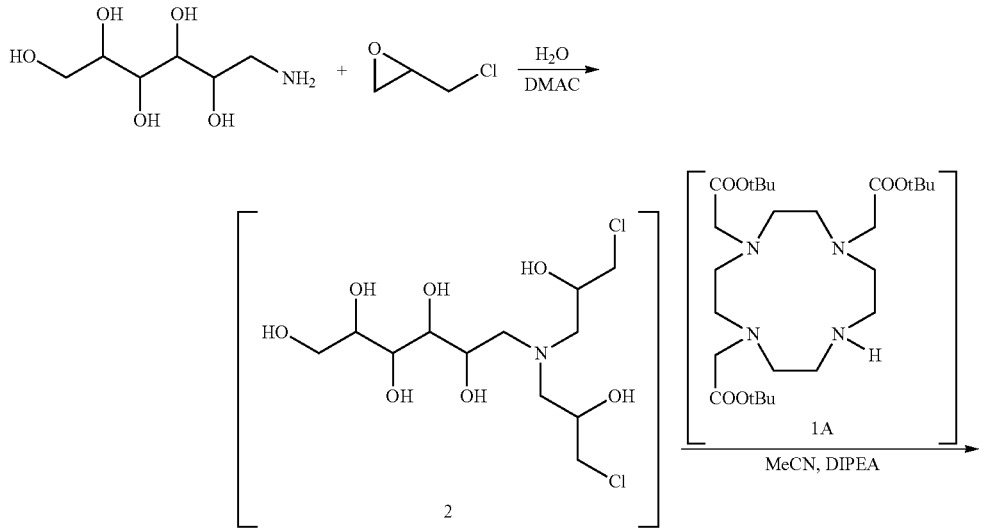

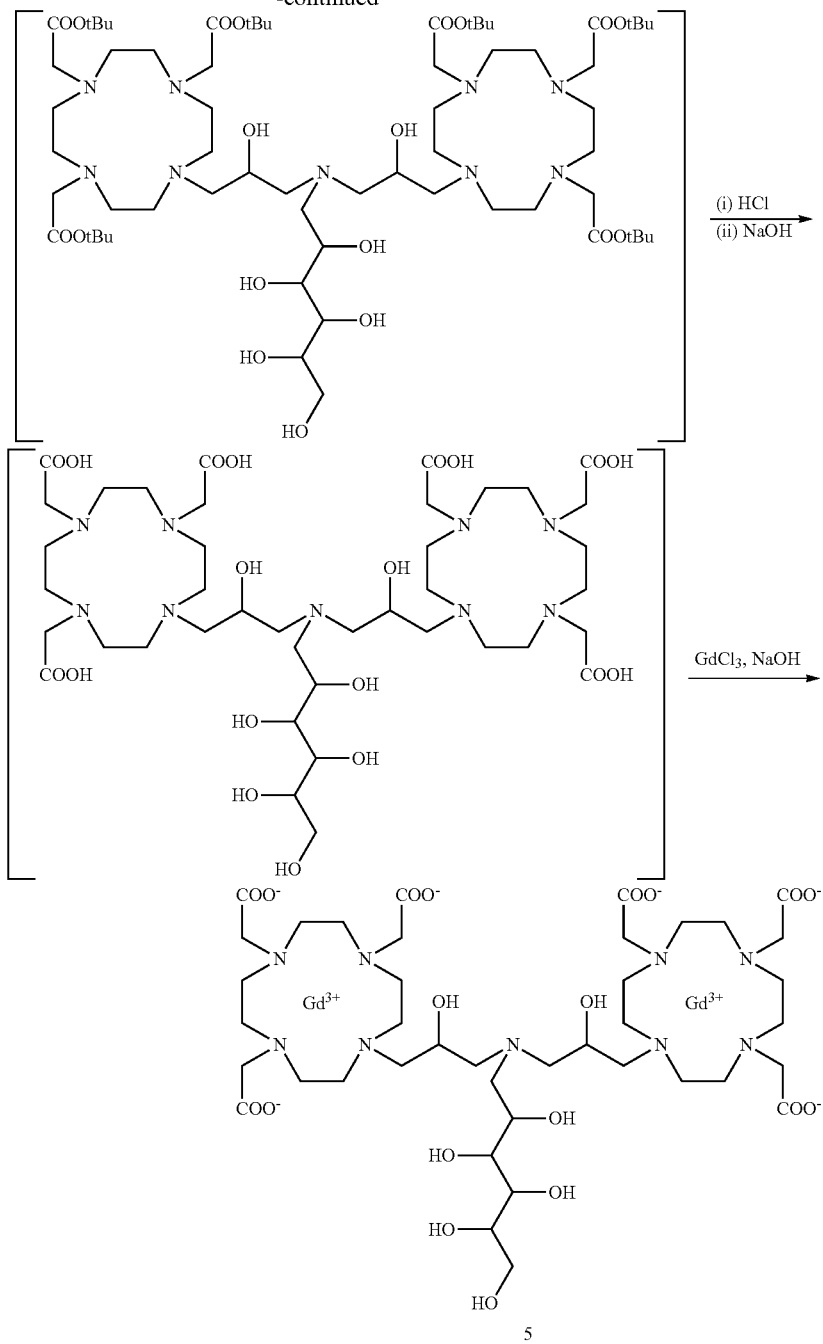

and the following steps:

a) Conversion of the Salt 1B to DO3A Tri-Tert-Butyl Ester 1A

DO3A 3t-Bu-HBr (236.68 g, 0.40 mol) was loaded into a reactor. MTBE (350.29 g) was added and the mixture was kept under vigorous stirring. An aqueous solution of KOH (50.67 g of KOH with assay 88%, 0.80 mol in 710.05 g of water) was loaded to the suspension and the mixture obtained was kept under stirring for 2 h at 23÷27° C. Then, the stirring was stopped in order to obtain the separation of two layers: upper organic layer and lower aqueous layer. The aqueous phase was discharged whilst the organic one was collected in a reactor. Quantitative yield.

a1) Solvent Changing Step with Isopropanol

To the organic solution of Example 2 a), isopropanol (160.70 g) was added and MTBE was completely removed by distillation. The assay of final solution of DO3A 3tBu was included in the range 56÷63% w/w. The 1A assay in solution was determined by an HPLC-UV method.

a2) Solvent Changing Step with MeCN

To the organic solution of Example 2 a), MeCN (160.70 g) is added and MTBE is completely removed by distillation. The assay of final solution of DO3A 3tBu is included in the range 56÷63% w/w. The 1A assay in solution was determined by an HPLC-UV method.

b) Synthesis of Intermediate 2

D-glucamine (40.0 g; 0.221 mol) in water (99.3 g) was dropped in a solution of epichlorohydrin (44.9 g; 0.486 mol) in DMAC (40.0 g; 0.043 L) at 24° C. in 2 h. The mixture was kept under stirring for 17 h, then DMAC was added (80.0 g; 0.085 L) and the water was distilled at 50° C. under vacuum to achieve a solution of the intermediate 2 in DMAC with a residual water content <2.0% w/w.

c) Alkylation of Compound 1A with Intermediate 2

DIPEA (65.3 g; 0.505 mol) and the solution of 1A obtained according to Example 2 a2) are added to the solution of the Intermediate 2 collected from Example 2 b) at 50° C. The mixture is further stirred at 70° C. for 72 h by monitoring the conversion by HPLC-UV method, then, after cooling to 25° C., it is diluted with 16% w/w ammonia aqueous solution (0.240 L). The resulting mixture is kept under stirring at 20° C. for 15 h obtaining precipitation of salts that are removed by filtration. The filtrate is then purified by chromatography on Amberlite XAD® 1600 (3 L; eluent: gradient of water/MeCN). Pure fractions (HPLC Area %>90) are collected and distilled to remove the organic solvent. The resulting residue is then concentrated at 50° C. under vacuum to give a solution of the protected ligand 3 in water with a final concentration of about 10% w/w that is used as such in the next step of the process.

d) Deprotection of Intermediate 3

34% hydrochloric acid aqueous solution (431.5 g; 4.023 mol) is added to the solution of Intermediate 3 from Example 2 c) by maintaining the temperature at 30÷35° C. At the end of the addition, the mixture is heated to 37° C. and kept under stirring for 36 h. Then the solution is cooled to 25° C. and neutralized by addition of 30% sodium hydroxide aqueous solution, the t-butanol formed as by-product is removed by distillation and the mixture is desalinated by nanofiltration. The mixture is then partially concentrated at 50° C. under vacuum up to concentration of 24% w/w and purified by chromatography on Amberlite XAD® 1600 (1 L; eluent water). The fractions selected by evaluation on HPLC-UV are treated with charcoal and concentrated at 50° C. under vacuum to obtain a 10% w/w water solution of the desired ligand 4 (0.075 mol), which is quantified by potentiometric titration using a copper sulfate solution as titrating agent.

e) Complexation

The solution of the deprotected ligand 4 obtained in Example 4 d) is heated to 37° C., then gadolinium chloride aqueous solution (140.5 g of solution; 39.5 g of gadolinium chloride; 0.150 mol) is added maintaining the temperature in the range 37÷43° C. At the end of the addition, the pH is adjusted to 5.3 by addition of 10% sodium hydroxide aqueous solution. The mixture is maintained at 40° C. for 2 h with formation of the respective paramagnetic complex 5. The presence of any free species is assessed e.g. by titration. The solution is then purified on Diaion CR11 chelating resin (0.16 L) reducing any free gadolinium content. After loading, the resin is washed with water, the pH adjusted to 5.5 and the solution concentrated under vacuum at 50° C. to obtain a 25% w/w water solution. This solution is loaded at pH 6 on Amberlite XAD® 1600 (3.3 L; eluent: gradient of water/MeCN). The fractions selected by evaluation on HPLC-FLD and UV are treated with charcoal and the resulting solution distilled at 50° C. under vacuum. The final solution (25% w/w) is spray-dried to isolate the gadolinium complex as a white powder (82.0 g corresponding to 74.6 g, as anhydrous product; titration assay: 99% w/w %, anhydrous base).

Overall yield from DO3A tri-tert-butyl ester 1A: 29%.

Example 3: Preparation of the Dimeric Compound 5

The dimeric complex compound 5 is obtained according to the synthetic procedure schematized in Example 2 and to the following steps:

b) Synthesis of Intermediate 2

D-glucamine (40.0 g; 0.221 mol) in water (100.0 g) was dropped in a solution of epichlorohydrin (44.9 g; 0.486 mol) in DMAC (40.0 g; 0.043 L) at 25° C. in 2 h. The mixture was kept under stirring for 16 h, then DMAC was added (80.0 g; 0.085 L) and the water was distilled at 50° C. under vacuum to achieve a solution of the intermediate 2 in DMAC with a residual water content <2.0% w/w.

c) Alkylation of Compound 1A with Intermediate 2

DIPEA (65.3 g; 0.505 mol) and the solution of 1A obtained according to Example 2 a2) are added to the solution of the Intermediate 2 collected from Example 3 step b) at 50° C. The mixture is further stirred at 75° C. for 70 h by monitoring the conversion by HPLC-UV method, then is partially concentrated at 60° C. under vacuum. After cooling to 23° C., a mixture of water (80.0 g) and MeCN (126.4 g; 0.160 L), previously prepared, and after 25% w/w ammonia aqueous solution (144.5 g; 0.160 L) are added. The resulting mixture is kept under stirring at 22° C. for 14 h. The mixture is filtered and purified by chromatography on Amberlite XAD® 1600 (3 L; eluent: gradient of water/MeCN). After elution the fractions with adequate purity (HPLC Area %>90) are collected, the organic solvent distilled, and the resulting solution concentrated at 50° C. under vacuum to give the protected ligand 3 in water solution (concentration: 13% w/w) which is used as such in the next step.

d) Deprotection of Intermediate 3

34% hydrochloric acid aqueous solution (435.0 g; 4.057 mol) is added to the solution of Intermediate 3 from Example 3 step c) by maintaining the temperature at 30÷35° C. At the end of the addition, the mixture is kept at 35° C. under stirring for 32 h. After, the solution is cooled to 23° C. and neutralized by addition of 30% sodium hydroxide aqueous solution, the t-butanol formed as by-product is removed by distillation and the mixture is desalinated by nanofiltration. The mixture is then partially concentrated at 50° C. under vacuum up to concentration of 22% w/w and purified by chromatography on Amberlite XAD® 1600 (1 L; eluent water). The fractions selected by evaluation with HPLC-UV are treated with charcoal and concentrated at 50° C. under vacuum to obtain a 25% w/w water solution of the desired ligand 4 (0.076 mol), which is quantified by potentiometric titration using a copper sulfate solution as titrating agent.

e) Complexation

To the solution of deprotected ligand 4 at 25° C., a gadolinium chloride aqueous solution (142.4 g of solution; 40.1 g of gadolinium chloride; 0.152 mol) is added maintaining the temperature in the range 23÷27° C. adjusting the pH to 7.0÷7.5 by addition of 30% sodium hydroxide aqueous solution. The mixture is maintained at 25° C. for 24 h with formation of the respective paramagnetic complex 5. The presence of any free species is assessed e.g. by titration. The resulting solution is purified on Amberlite XAD® 1600 (3.3 L; eluent: gradient of water/MeCN). The fractions selected by evaluation on HPLC-FLD and UV are treated with charcoal and the resulting solution distilled at 50° C. under vacuum. The final solution (25% w/w) is spray-dried to isolate the gadolinium complex as a white powder (73.5 g corresponding to 66.9 g, as anhydrous product; titration assay: 99% w/w %, anhydrous base).

Overall yield from DO3A tri-tert-butyl ester 1A: 26%.

Analogous results as the ones of Examples 2 and 3 above can be obtained by carrying out similar procedures, for example as disclosed in the co-pending application PCT/EP2021/070801.

The invention claimed is:
1. A process for the manufacturing of a dimeric complex of formula 5

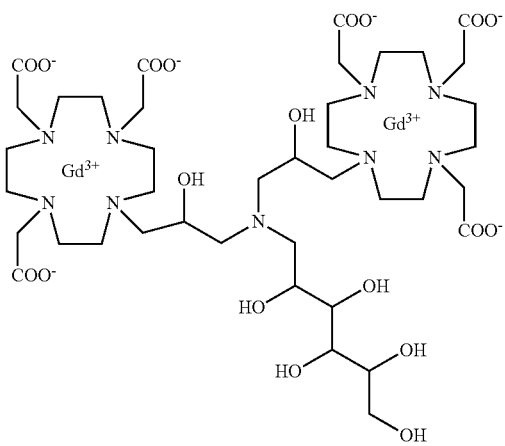

comprising the following steps:
a) admixing a salt of formula 1B

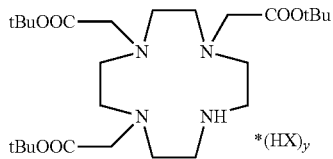

wherein X is bromide, and y is 1;
with a basic aqueous solution and an organic solvent immiscible with the basic aqueous solution, to provide a heterogenous mixture comprising the salt of formula 1B, wherein the organic solvent is methyl tert-butyl ether (MTBE);
b) converting the salt of formula 1B comprised in the heterogenous mixture of step a), to provide a heterogenous mixture comprising DO3A tri-tert-butyl ester of formula 1A

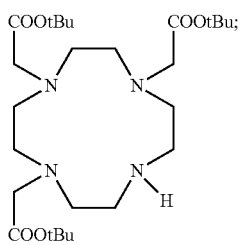

c) collecting the organic solvent from the heterogenous mixture of step b), to obtain an organic solution comprising DO3A tri-tert-butyl ester 1A;
d) preparing a solution comprising a compound of formula 2

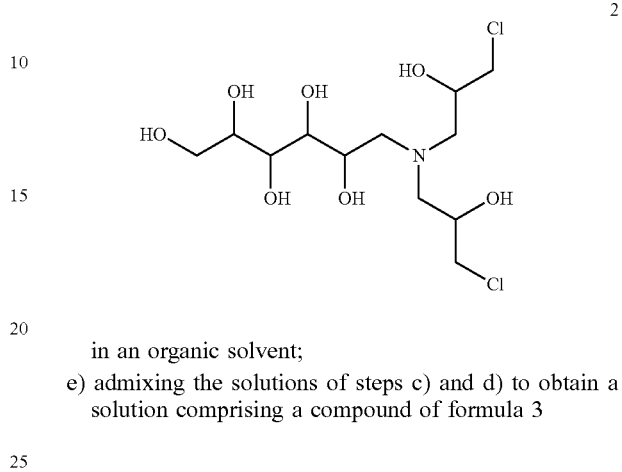

in an organic solvent;
e) admixing the solutions of steps c) and d) to obtain a solution comprising a compound of formula 3

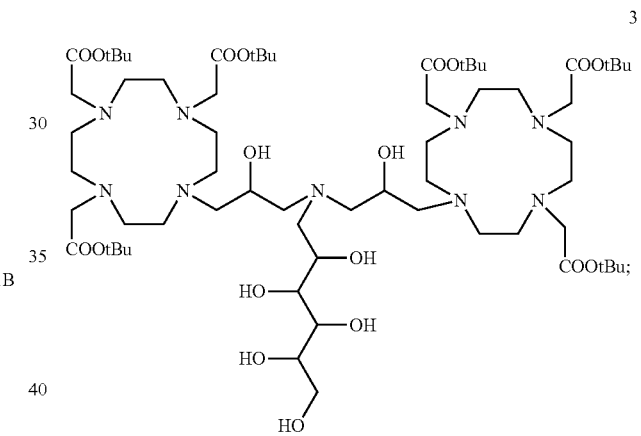

f) without isolating the compound from the solution of step e), removing the tert-butyl protecting groups from the compound of formula 3 to obtain a solution comprising a free ligand of formula 4

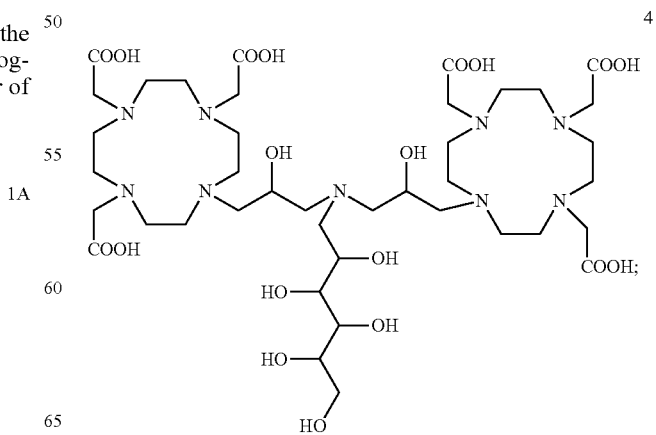

g) without isolating the free ligand of formula 4, adding gadolinium metal ions to the solution of step f) to obtain a solution comprising the dimeric complex of formula 5; and h) isolating the dimeric complex of formula 5, wherein the solvent in all the steps following the obtaining of the compound of formula 3 is an aqueous solvent.

2. The process according to claim 1, wherein the amount of organic solvent in step a) is 1.0 to 5.0 w/w with respect to the amount of salt 1B.

3. The process according to claim 2, wherein the amount of organic solvent in step a) is 1.2 to 3.0 w/w with respect to the amount of salt 1B.

4. The process according to claim 3, wherein the amount of organic solvent in step a) is 1.4 to 1.6 w/w with respect to the amount of salt 1B.

5. The process according to claim 4, wherein the amount of organic solvent in step a) is 1.5 w/w with respect of the amount of salt 1B.

6. The process according to claim 1, wherein the basic aqueous solution comprises a base selected from the group consisting of KOH, NaOH, $Na_2CO_3$, and $K_2CO_3$.

7. The process according to claim 6, wherein the base is in a molar ratio of 1.0 to 4.0 mol with respect to 1 mol of salt 1B.

8. The process according to claim 7, wherein the base is in a molar ratio of 1.2 to 3.0 mol with respect to 1 mol of salt 1B.

9. The process according to claim 8, wherein the base is in a molar ratio of 1.7 to 2.3 mol with respect to 1 mol of salt 1B.

10. The process according to claim 9, wherein the base is in a molar ratio of 2.0 mol with respect to 1 mol of salt 1B.

11. The process according to claim 1, wherein the amount of basic aqueous solution in step a) is 2.0 to 10.0 w/w with respect to the amount of salt 1B.

12. The process according to claim 11, wherein the amount of basic aqueous solution in step a) is 2.2 to 6.0 w/w with respect to the amount of salt 1B.

13. The process according to claim 12, wherein the amount of basic aqueous solution in step a) is 2.8 to 3.2 w/w with respect to the amount of salt 1B.

14. The process according to claim 13, wherein the amount of basic aqueous solution in step a) is 3.0 w/w with respect to the amount of salt 1B.

15. The process of claim 1, wherein step d) comprises reacting D-glucamine with epichlorohydrin, to obtain a solution comprising the compound of formula 2 in an organic solvent.

16. The process of claim 15, wherein step d) comprises:
d1) adding an aqueous solution comprising D-glucamine to a solution comprising epichlorohydrin in an organic solvent, to give the compound of formula 2 in a water/organic solvent mixture, wherein the amount of epichlorohydrin is in an excess over the stoichiometric amount; and d2) removing the water from the mixture, to obtain a solution comprising the compound of formula 2 in the organic solvent.

17. The process of claim 1, wherein step e) comprises:
e1) reacting the compound of formula 2 from step d) with DO3A tri-tert-butyl ester 1A from step c) in the presence of a base to give an organic crude solution comprising a compound of formula 3;

e2) diluting the obtained organic crude solution with water, a water/organic solvent mixture, or an aqueous solution to obtain a water/organic crude;

e3) purifying the water/organic crude, preferably by chromatography, to obtain the compound of formula 3 in a water/organic solvent mixture, and e4) removing the organic solvent from the mixture to obtain an aqueous solution comprising the compound of formula 3.

18. The process of claim 1, wherein step f) comprises:
f1) adding an acid to an aqueous solution comprising the compound of formula 3 from step e) to remove the protecting tert-butyl groups and obtain an acidic aqueous solution comprising the free ligand of formula 4;

f2) adding a base to the acidic aqueous solution obtained from step f1) to obtain a neutral aqueous solution comprising the free ligand of formula 4;

f3) purifying and then optionally concentrating the neutral aqueous solution obtained from step f2) to obtain an aqueous solution comprising the free ligand of formula 4.

19. The process of claim 18, wherein step f3) comprises: distilling the neutral solution for removing the formed t-butanol; desalinating the distillation residue to obtain a desalinated solution; purifying by chromatography the desalinated solution to obtain an aqueous solution comprising the ligand of formula 4; and optionally concentrating the aqueous solution.

20. The process of claim 1, wherein step g) comprises:
g1) adding a gadolinium salt to the solution comprising the ligand of formula 4 from step f) to obtain a solution comprising the dimeric complex of formula 5;

g2) purifying the solution from step g1) by chromatography; and g3) concentrating the purified solution from step g2).

21. The process of claim 1, wherein step h) comprises isolating the dimeric complex of formula 5 as a white solid by spray drying of the solution directly collected from step g).

* * * * *